United States Patent [19]
Ishida et al.

[11] Patent Number: 6,093,858
[45] Date of Patent: Jul. 25, 2000

[54] METHOD FOR PRODUCING BIS (TRIFLUOROMETHYL) BENZENE

[75] Inventors: Michio Ishida; Makoto Koide; Yutaka Katsuhara, all of Saitama, Japan

[73] Assignee: Central Glass Company, Limited, Ube, Japan

[21] Appl. No.: 09/300,260

[22] Filed: Apr. 27, 1999

[30] Foreign Application Priority Data

Apr. 27, 1998 [JP] Japan .................................. 10-117013

[51] Int. Cl.[7] ........................... C07C 22/00; C07C 17/00
[52] U.S. Cl. ...................................... 570/145; 204/157.97
[58] Field of Search ....................... 570/145; 204/157.97

[56] References Cited

U.S. PATENT DOCUMENTS

| | | |
|---|---|---|
| 2,654,789 | 10/1953 | Ligett . |
| 2,859,245 | 11/1958 | Smith . |
| 4,079,089 | 3/1978 | Klauke . |
| 4,462,937 | 7/1984 | Ramanadin et al. .................... 570/145 |
| 4,966,988 | 10/1990 | Schinski et al. . |

FOREIGN PATENT DOCUMENTS

077853 A1   5/1983   European Pat. Off. .

OTHER PUBLICATIONS

Marsh, F.D., Farnham, W.B., Sam, D.J., and Smart, B.E. (1982) "Dichlorine Monoxide: A Powerful and Selective Chlorinating Reagent". *J. Am. Chem. Soc.* 104:4680–4682.

Anonymous (1985) "Preparation of Methyl Substituted Trifluoromethylbenzenes". Research Disclosure 255:368.

Murray, R.L., Beanblossom, W.S., and Wojcik, B.H., (1947) "Production of Bis (Trifluoromethyl) Benzene". *Industrial and Engineering Chemistry* 39:302–305.

McBee, Earl T., Frederick, Marvin R., (1949) "Chlorination of bis– and Chloro–bis–(perfluoroalkyl)–benzenes" *J. Am. Chem. Soc.* 71:1490–1491.

*Primary Examiner*—Alan Siegel
*Attorney, Agent, or Firm*—Evenson, McKeown, Edwards & Lenanhan, P.L.L.C.

[57] ABSTRACT

The invention relates to a method for producing a bis (trifluoromethyl)benzene. This method includes the steps of (a) chlorinating a compound represented by the general formula (1) by chlorine, thereby to produce a trichloromethyltrifluoromethylbenzene; and (b) fluorinating the tricbloromethyltrifluoromethylbenzene by hydrogen fluoride, thereby to produce the bis(trifluoromethyl)benzene,

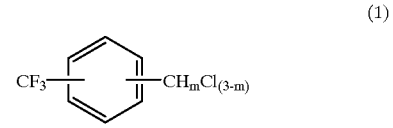

(1)

where m is 1, 2 or 3. It is not necessary in the invention to handle solid in any reaction step. Therefore, the invention is very useful in the production of a bis(trifluoromethyl) benzene in an industrial scale

7 Claims, No Drawings

METHOD FOR PRODUCING BIS (TRIFLUOROMETHYL) BENZENE

BACKGROUND OF THE INVENTION

The present invention relates to methods for producing bis(trifluoromethyl)benzene which is useful as an intermediate of medicines and agricultural chemicals, a raw material of functional substances, a reaction solvent, a washing solvent, etc.

Murray et al. (Industrial and Engineering Chemistry, Vol. 39 [1947] No. 3, pp.302–305) disclose a method for producing bis(trifluoromethyl)benzene, comprising the steps of (a) chlorinating xylene to bis(trichloromethyl)benzene; and (b) fluorinating the bis(trichloromethyl)benzene to bis (trifluoromethyl)benzene. McBee et al. (J Am. Chem. Soc., Vol. 71 [1949] pp. 1490–1491) disclose the production of bis(trifluoromethyl)benzene from the corresponding bis (trichloromethyl)benzene by fluorination with anhydrous hydrogen fluoride in the presence of antimony(V) chloride at room temperature. Smith et al. (U.S. Pat. No. 2,859,245) disclose a method for producing 1,4-bis(trifluoromethyl) benzene by fluorinating terephthalic acid by sulfur tetrafluoride at 100° C. and then 120° C.

SUMMARY OF THE INVENTION

A compound used in the production of 1,4-bis (trifluoromethyl)benzene, that is, 1,4-bis(trichloromethyl) benzene, has a high melting point of 111° C. and thus is in the form of solid at normal temperature or room temperature. Therefore, upon its use, for example, it is melted at high temperature or dissolved in solvent.

It is therefore an object of the present invention to provide a method for easily producing a bis(trifluoromethyl) benzene, in which method it is not necessary to treat or handle solid in any reaction step.

According to the present invention, there is provided a method for producing a bis(trifluoromnethyl)benzene. This method comprises (a) chlorinating a compound represented by the general formula (1) by chlorine, thereby to produce a trichloromethyltrifluoromethylbenzene; and (b) fluorinating the trichloromethyltrifluoromethylbenzene by hydrogen fluoride, thereby to produce the bis(trifluoromethyl)benzene,

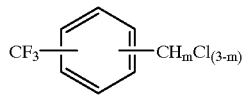

(1)

where m is 1, 2 or 3.

In the invention, it is optional to omit the fluorination if the trichloromethyltrifluoromethylbenzene is the final product. Furthermore, it is optional in the invention to omit the chlorination if the trichloromethyltrifluoromethylbenzene is used as a raw material in the production of the bis (trifluoromethyl)benzene.

DESCRTPTION OF THE PREFERRED EMBODIMENTS

In general, if xylene is chlorinated by chlorine, it is possible to obtain a compound in which an arbitrary number of hydrogen atoms of the two methyl groups has been replaced with chlorine atoms. For example, it is possible to obtain 1,4-bis(trichloromethyl)benzene as a major reaction product by chlorinating para-xylene with chlorine at a sufficiently high temperature of about 150–170° C., in the presence of photocatalyst or another catalyst such as benzamide. In a method not according to the invention, the obtained 1,4-bis(trichloromethyl)benzene may be separated from the reaction products of this chlorination, and then only the residue of the reaction products, that is, insufficiently chlorinated compounds (e.g., 1-dichloromethyl-4-trichloromethylbenzene), may be subjected again to the above chlorination, thereby to produce 1,4-bis (trichloromethyl)benzene. After that, the total of the 1,4-bis (trichloromethyl)benzene may be fluorinated in this method by hydrogen fluoride to 1,4-bis(trifluoromethyl)benzene. This method not according to the invention is, however, not preferable, since it is necessary to fluorinate a compound (i.e., 1,4-bis(trichloromethyl)benzene) that is high in melting point and thus in the form of solid at normal temperature.

In contrast, according to the invention, it is not necessary to handle solid in any reaction step in the production of a bis(trifluoromethyl)benzene, as will be clarified hereinafter. A method for producing a bis(trifluoromethyl)beuzene will be described in detail in accordance with the invention. In case that, for example, para-xylene is used as a starting raw material in the production of a bis(trifluoromethyl)benzene, a mixture of 1,4-bis(trichloromethyl)benzene and 1-dichloromethyl-4-trichloromethylbenzene can be obtained by chlorinating para-xylene by chlorine. The present inventors have unexpectedly found that this mixture has a relatively low melting point of not higher than 60° C. Then, hydrogen fluoride can be supplied to the obtained mixture that is in the form of liquid, thereby to respectively fluorinate the 1,4-bis(trichloromethyl)benzenae and the 1-dichloromethyl-4-tirchloromethylbenzene to 1,4-bis (trifluoromethyl)benzene and 1-dichloromethyl-4-trifluoromethylbenzene. After that, this 1-dichloromethyl-4-trifluoromethylbenzene can be separated from the 1,4-bis (trifluoromethyl)benzene through distillation etc. Then, the 1-dichloromethy-4-trifluoromethylbenzene obtained as a by-product, which can be represented by the general formula (1) where m is 1, can easily be chlorinated to 1-trichloromethyl-4-trifluoromethylbenzene, and the obtained 1-trichloromethyl-4-trifluoromethylbenxzene can be fuorinated to 1,4-bis(trifluoromethyl)benzene. Thus, it is not necessary in the invention to handle solid in any reaction step in the production of a bis(trifluoromethyl)benzene. With this, the chlorination can be conducted at a relatively low temperature. Therefore, the invention is very useful in the production of a bis(trifluoromethyl)benzene in an industrial scale.

According to a preferred embodiment of the invention, the compound represented by the general formula (1) is represented by the following general formula (2), the trichloromethyltrifluoromethylbenzene is 1-trichloromethyl-4-trifluoromethylbenzene, and the bis(trifluoromethyl) benzene is 1,4-bis(tifluoromethyl)benzene, as described hereinabove,

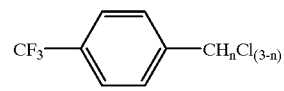

(2)

where n is 1, 2 or 3.

In the invention, the chlorination is conducted by bringing the compound represented by the general formula (1) and chlorine into contact with each other in a reaction zone. This reaction zone is preferably provided by a reaction vessel made of glass, stainless steel, or a material lined with glass or fluororesin. The manner of contact therebetween for the chlorination is not particularly limited, and the chlorination can be conducted by a continuous operation, a batch operation, or a half-batch operation in which only the reaction products are continuously removed from the reaction vessel. For example, the chlorination is preferably conducted by allowing chlorine gas to flow into the reaction vessel charged with the compound represented by the general formula (1). The chlorination is conducted preferably in the presence of a catalyst or under an irradiation with light. Examples of this catalyst are azo-compounds such as azobisisobutyronitrile and azobisaleronitrile, radical initiators such as peroxides, for example, benzoyl peroxide, dodecanoyl peroxide, dilauroyl peroxide and t-butylperoxypivalate, and phosphorus compounds such as red phosphorus, phosphorus pentachloride, phosphorus trichloride, triphenylphosphine and triphenyl phosphite. The reaction temperature of the chlorination may vary depending on the type of catalyst and is preferably of about 0–120° C., still preferably of 40–100° C., more still preferably of 50–80° C. It may also vary depending on the number of chlorine atoms of the compound represented by the general formula (1). If it is lower than 0° C., the reaction may nearly not proceed. If it is higher than 120° C., the yield may become too low. Since the chlorination is an exothermic reaction, the reaction temperature may be adjusted by heating or cooling the reaction vessel from outside, by changing the flow rate of the chlorine gas into the reaction vessel, and/or by diluting the chlorine gas with an inert gas. The reaction pressure has almost no influence on the chlorination, and the pressurization thereto is not particularly needed. It may be of 0.5–10 kg/cm$^2$, preferably of 1–3 kg/cm$^2$.

In the chlorination, it suffices to provide the chlorine gas in an amount of at least m moles, particularly of about m to 2 m, where m is the same as that of the general formula (1), relative to 1 mole of the compound represented by the general formula (1). The amount of the chlorine gas can be about m moles, where m is defined as above, by optimizing the reaction apparatus or operations. For example, the amount of the chlorine gas may be of 1–2 moles and can be about 1 mole by the optimization thereof, relative to 1 mole of 1-dichloromethyl-4-trifluoromethylbenzene. Furthermore, it may be of 2–4 moles and can be about 2 moles by the optimization thereof, relative to 1 mole of 1-chloromethyl-4-trifluoromethylbenzene. Since the chlorination is a gas-liquid contact reaction, it may be effective to take conventional measures for improving the efficiency of the contact therebetween, such as the uses of stirrer, the chlorine gas blow device, sparger, etc., and the multi-stage chlorination.

In the invention, the chlorination for chlorinating a compound represented by the general formula (1) may be conducted in the presence of a solvent. This solvent is preferably capable of dissolving this compound and the product of this chlorination, is preferably inert in the chlorination, and preferably has a boiling point that is sufficiently different from the product of this chlorination. Examples of the solvent are carbon tetrachloride, chloroform, tetrachloroethane, monochlorobenzene, o-, m- and p-dichlorobenzenes, trichlorobenzene, monobromobenzene, dibromobenzene, 2,3-, 2,4-, 2,5-, 2,6-, 3,4-, 3,5-dichlorobenzotrifluorides, 3,4,5-trichlorobenzotrifluoride, and bis(trifluoromethyl)benzene.

In the invention, the product of the chlorination, that is, trichloromethyltrifluoromethylbenzene, may be purified by a common purification, such as distillation, to a high-purity product. This purification is, however, not particularly necessary, in case that the product of the chlorination is used as a raw material of the subsequent fluorination.

In the invention, the fluorination can be conducted by bringing trichloromethyltrifluoromethylbenzene and hydrogen fluoride into contact with each other in the presence of no catalyst or a catalyst, that is, a metal halide (e.g., antimony pentachloride and tin tetrachloride), which is commonly used in a liquid-phase fluorination. If a catalyst is used in the fluorination, the reaction may proceed at a temperature of at least 0° C. In this case, it may be necessary to conduct the fluorination at a temperature of not higher than room temperature in order to adjust the reaction rate. In contrast, if catalyst is not used in the fluorination, the reaction temperature may be of 40–150° C., preferably of 50–1OO° C. If it is lower than 40° C., the reaction rate may become too low, thereby to make the production efficiency inferior. If it is higher than 150° C., the yield of bis (trifluoromethyl)benzene may become too low by the formation of polymerizable substances. In the fluorination, the amount of hydrogen fluoride is preferably of 3–50 moles, more preferably of 3–20 moles, per mole of trichloromethyltrifluoromethylbenzene.

In the invention, the fluorination for fluorinating trichloromethyltrifluoromethylbenzene may be conducted by using a stirrer in a pressure resistant container made of a material, such as Monel metal, Hastelloy or nickel, or a material lined with one of these metals or a fluororesin such as polytetrafluoroethylene or perfluoroalkylvinylether resin. The fluorination may be conducted by a batch operation, a continuous operation, or a half-batch operation in which only the reaction product is continuously removed from the reactor. The reaction pressure of the fluorination may be of 1–100 kg/cm$^2$, preferably not higher than 30 kg/cm$^2$ from the viewpoint of the limitation of the material for the reactor. If it is lower. than 1 kg/cm$^2$, hydrogen fluoride may not liquefy at the above-mentioned preferable temperature. This may stop the fluorination. It is optional to use in the fluorination an inert solvent such as the aimed product, 1-4-bis (trifluoromethyl)benzene.

The following nonlimitative examples are illustrative of the present invention.

EXAMPLE 1

In this example, the chlorination of the invention was conducted as follows. At first, a 1-liter, four-necked, glass flask equipped with a stirrer and a reflux condenser was charged with 620 g of 1-dichloromethyl-4-trifluoromethylbenzene (liquid). Then, nitrogen gas was slowly bubbled into this liquid with stirring, and it was started to increase the temperature of the reaction liquid. When the temperature of the reaction liquid reached 70° C., the introduction of nitrogen gas was stopped, and 4.5 g of 2,2'-azobisisobutyronitrile (AIBN) was introduced into the flask. 15 minutes after that, it was started to supply chlorine gas at a rate of 38 g/hr. This time was defined as the reaction starting time. During the reaction, the gas flowing out of the flask was exhausted by passing it through a water trap and then a sodium hydroxide aqueous solution trap. After that, while the reaction temperature was maintained at a temperature of 75–80° C., the reaction was continued for 7 hr by adding 2.2 g of AIBN at intervals of 2 hr. Then, the introduction of chlorine gas was stopped After that, the reactor was cooled down to room temperature by introducing nitrogen gas. The contents of the reactor after the reaction were in an amount of 687 g and found by an analysis with gas chromatograph to contain 96.3% of 1-trichloromethyl-4-trifluoromethylbenzene and 1.6% of 1-dichloromethyl-4-trifluoromethylbenzene. These percentages and those of the after-mentioned examples are areal percentages in chromatogram.

EXAMPLE 2

In this example, the chlorination of the invention was conducted as follows. At first, first and second 100-ml, four necked, glass flasks, each being equipped with a stirrer and a reflux condenser, were prepared. Then, the first flask was provided with an insert pipe for bubbling chlorine gas from a chlorine gas cylinder. The second flask was provided with an insert pipe for bubbling a gas flowing out of the reflux condenser of the first flask. Then, each of the first and second flasks was charged with 121 g of 1-dichloromethyl-4-trifluoromethylbenzene (liquid). Then, nitrogen gas was slowly bubbled with stirring into this liquid from the insert pipe, and it was started to increase the temperature of the reaction liquid. When the temperature of the reaction liquid reached 65° C., the introduction of nitrogen gas was stopped, and 0.174 g of AIBN was introduced into the flask. 15 minutes after that, it was started to supply chlorine gas. This time was defined as the reaction starting time. During the reaction, the gas flowing out of each reactor was exhausted by passing it through a water trap and then a sodium hydroxide aqueous solution trap. After that, while the reaction temperature was maintained at a temperature of 65–70° C. the reaction was continued for 8.5 hr by adding 0.174 g of AIBN into each reactor at intervals of 2 hr. Then, the introduction of chlorine gas was stopped. After that, the reactor was cooled down to room temperature by introducing nitrogen gas for 1 hr. The chlorine gas was introduced at an average rate of 6 g/hr. The contents of the first flask after the reaction were in an amount of 139 g and found by an analysis with gas chromatograph to contain 98.4% of 1-trichloromethyl-4-trifluoromethylbenzene and 0.7% of 1-dichloromethyl-4-trifluoromethylbenzene. The contents of the second flask after the reaction were in an amount of 130 g and found by an analysis with gas chromatograph to contain 44.8% of 1-trichloromethyl-4-trifluoromethylbenzene and the unreacted 1-dichloromethyl-4-trifluoromethylbenzene.

EXAMPLE 3

In this example, the fluorination of the invention was conducted as follows. At first, a 50-ml stainless steel autoclave equipped with a reflux condenser was charged with 15 g of 1-trichloromethyl-4-trifluoromethylbenzene (purity: 98.4%) obtained in Example 2 and 10 g of anhydrous hydrogen fluoride. After closing the autoclave, the reaction was started, and the temperature of the reaction liquid was gradually increased to 60° C. As this temperature increased, the internal pressure increased. When it reached 11 kg/cm$^2$, a needle valve provided on the outlet side of the reflux condenser was slowly opened, thereby to adjust the internal pressure to 9 kg/cm$^2$. After that, this adjustment of the internal pressure was repeated until the liquid temperature reached 85° C. by gradually increasing the liquid temperature for 7 hr. 7 hr after the start of the reaction, the increase of the internal pressure was stopped, and at this time the autoclave was cooled down. Then, its pressure was released. After that, the reaction liquid of the autoclave was introduced into a container charged with ice. Then, the organic matter of the reaction liquid was separated from the water phase. The obtained organic matter was in an amount of 10.54 g and was found by an analysis with gas chromatograph to contain 97.6% of 1,4-bis(trifluoromethyl)benzene and 0.05% of 1-dichloromethyl-4-trifluoromethylbenzene.

The entire disclosure of Japanese Patent Application No. 10-117013 filed on Apr. 27, 1998, of which priority is claimed in is the application, including specification, claims, and summary, is incorporated herein by reference in its entirety:

What is claimed is:

1. A method for producing bis(trifluoromethyl)benzene, said method comprising:

chlorinating xylene by chlorine, thereby obtaining a mixture of bis(trichloromethyl)benzene and dichloromethyltrichloromethylbenzene;

supplying hydrogen fluoride to said mixture, thereby respectively fluorinating said bis(trichloromethyl) benzene and said dichloromethyltrichloromethylbenzene to bis(trifluoromethyl)benzene and dichloromethyltrifluoromethylbenzene;

separating said dichloromethyltrifluoromethylbenzene from said bis(trifluoromethyl)benzene;

chlorinating said dichloromethyltrifluoromethylbenzene by chloride thereby producing trichloromethyltrifluoromethylbenzene; and fluorinating said trichloromethyltrifluoromethylbenzene by hydrogen fluoride, thereby producing bis (trifluoromethyl)benzene.

2. A-method for producing trichloromethyltrifluoromethylbenzene, said method comprising:

chlorinating xylene by chlorine, thereby obtaining dichloromethyltrichloromethylbenzene;

fluorinating said dichloromethyltrichloromethylbenzene by hydrogen fluoride, thereby obtaining dichloromethyltrifluoromethylbenzene; and chlorinating said dichloromethyltrifluoromethylbenzene by chlorine thereby obtaining said trichloromethyltrifluoromethylbenzene.

3. A method according to claim 2, wherein said hydrogen fluoride is a liquid.

4. A method according to claim 2, wherein no compound is a solid.

5. A method according to claim 2, wherein said chlorinating said dichloromethyltrifluoromethylbenzene is conducted in the presence of a radical initiator or under an irradiation with light, at a reaction temperature of 0–120° C., and wherein said chlorine in said chlorinating said dichloromethyltrifluoromethylbenzene is in an amount of at least 1 mole relative to 1 mole of said dichloromethyltrifluoromethylbenzene.

6. A method according to claim 2 wherein said chlorinating said dichloromethyltrifluoromethylbenzene is conducted in the presence of a catalyst of azobisisobutyronitrile at a reaction temperature of 0–120° C.

7. A method for producing 1,4-bis(trifluoromethyl) benzene, said method comprising:

chlorinating para-xylene by chlorine, thereby to obtain a mixture of 1,4-bis(trichloromethyl)benzene and 1-dichloromethyl-4-trichloromethylbenzene;

supplying hydrogen fluoride to said xnixture, thereby to respectively fluorinate said 1,4-bis(trichloromethyl) benzene and said 1-dichloromethyl-4-trichloromethylbenzene to 1,4-bis(trifluoromethyl) benzene and 1-dichloromethyl-4-trifluoromethylbenzene;

separating said 1-dichloromethyl-4-trifluoromethylbenzene from said 1,4-bis (trifluoromethyl)benzene;

chlorinating said 1-dichloromethyl-4-trifluoromethylbenzene by chlorine, thereby to produce 1-trichloromethyl-4-trifluoromethylbenzene; and fluorinating said 1-trichloromethyl-4-trifluoromethylbenzene by hydrogen fluoride, thereby to produce 1,4-bis(trifluoromethyl)benzene.

* * * * *